(12) United States Patent
Contente

(10) Patent No.: US 6,264,638 B1
(45) Date of Patent: *Jul. 24, 2001

(54) INTRAVAGINAL DRUG DELIVERY SYSTEM AND DISCHARGE COLLECTION DEVICE

(75) Inventor: Audrey Contente, New York, NY (US)

(73) Assignee: Ultrafem, Inc., Missoula, MT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/828,962

(22) Filed: Mar. 28, 1997

Related U.S. Application Data

(60) Continuation-in-part of application No. 08/215,062, filed on Mar. 21, 1994, which is a division of application No. 07/904,367, filed on Jun. 26, 1992, now Pat. No. 5,295,984, which is a continuation-in-part of application No. 07/817,498, filed on Jan. 7, 1992, now abandoned, which is a division of application No. 07/446,553, filed on Dec. 7, 1989, now abandoned, said application No. 07/904,367, is a continuation-in-part of application No. 07/865,746, filed on Apr. 10, 1992, now abandoned, said application No. 07/904,367, is a continuation-in-part of application No. 07/852,265, filed on Jun. 8, 1992.

(51) Int. Cl.⁷ ..................................................... A61M 31/00
(52) U.S. Cl. ........................... 604/285; 604/330; 128/832
(58) Field of Search .................................... 604/317, 285, 604/327–328, 330, 331, 358; 128/760, 767, 769, 834, 837, 838, 884, 841, 887, 532

(56) References Cited

U.S. PATENT DOCUMENTS

| | | |
|---|---|---|
| 71,414 | 11/1867 | Rohleder . |
| 1,083,721 | 1/1914 | Asch . |
| 1,891,761 | 12/1932 | Goddard . |

(List continued on next page.)

FOREIGN PATENT DOCUMENTS

| | | |
|---|---|---|
| 5471 | 12/1931 | (AU) . |
| 205896 | 1/1909 | (DE) . |
| 256410 | 2/1913 | (DE) . |
| 444367 | 5/1927 | (DE) . |
| 553547 | 6/1932 | (DE) . |
| 620530 | 10/1935 | (DE) . |
| 845832 | 8/1952 | (DE) . |
| 134671 | 3/1985 | (EP) . |
| 2388545 | 11/1978 | (FR) . |
| 260600 | 10/1926 | (GB) . |
| 87/01581 | 3/1987 | (WO) . |
| WO 89/00415 | 1/1989 | (WO) . |

*Primary Examiner*—Glenn K. Dawson
(74) *Attorney, Agent, or Firm*—Dickstein Shapiro Morin & Oshinsky LLP

(57) ABSTRACT

A device is provided for reliably, comfortably and conveniently introducing agents, including drugs and other substances, into the vaginal canal. A discharge collection device is also disclosed. The disclosed devices may be formed of an elastomeric rim and a flexible film. The rim may have a non-circular cross section. The film may be collapsible into a low profile insertion configuration. The devices may be disposable, and may be constructed so as to be convenient to use, comfortable to wear internally, and reliable. Preferably, the devices are formed of thermoplastic material that softens in response to body temperature to provide improved comfort and handling.

18 Claims, 9 Drawing Sheets

U.S. PATENT DOCUMENTS

| | | |
|---|---|---|
| 1,986,504 | 12/1935 | Cubbon . |
| 1,996,242 | 4/1935 | Hagedorn . |
| 2,024,539 | 12/1935 | Schmid . |
| 2,061,384 | 11/1936 | Manegold . |
| 2,079,022 | 5/1937 | Martin . |
| 2,234,494 | 3/1941 | Lay . |
| 2,324,656 | 7/1943 | Vincent . |
| 2,443,943 | 6/1948 | Young . |
| 2,529,363 | 11/1950 | Ballard et al. . |
| 2,534,900 | 12/1950 | Chalmers . |
| 2,616,426 | 11/1952 | Gordon . |
| 2,697,057 | 12/1954 | Senger et al. . |
| 2,915,065 | 12/1959 | Lyons et al. . |
| 3,036,570 | 5/1962 | Milgrom et al. . |
| 3,037,508 | 6/1962 | Friedman . |
| 3,042,029 | 7/1962 | Johansson . |
| 3,060,931 | 10/1962 | Clark . |
| 3,128,767 | 4/1964 | Nolan . |
| 3,169,522 | 2/1965 | Monett . |
| 3,216,422 | 11/1965 | Steiger et al. . |
| 3,404,682 | 10/1968 | Waldron . |
| 3,626,942 | 12/1971 | Waldron . |
| 3,841,333 | 10/1974 | Zalucki . |
| 3,845,766 | 11/1974 | Zöller . |
| 3,854,480 | 12/1974 | Zaffaroni . |
| 3,983,874 | 10/1976 | Davis et al. . |
| 4,012,496 | 3/1977 | Schöpflin et al. . |
| 4,031,886 | 6/1977 | Morhenn . |
| 4,093,490 | 6/1978 | Ziets et al. . |
| 4,198,965 | 4/1980 | Strickman et al. . |
| 4,198,976 | 4/1980 | Drobish et al. . |
| 4,200,090 | 4/1980 | Drobish . |
| 4,219,016 | 8/1980 | Drobish et al. . |
| 4,232,673 | 11/1980 | Bucalo . |
| 4,261,352 | 4/1981 | Sedlacek . |
| 4,286,587 | 9/1981 | Wong . |
| 4,286,593 | 9/1981 | Place et al. . |
| 4,300,544 | 11/1981 | Rudel . |
| 4,304,226 | 12/1981 | Drobish et al. . |
| 4,311,543 | 1/1982 | Strickman et al. . |
| 4,320,751 | 3/1982 | Loeb . |
| 4,326,510 | 4/1982 | Buckles . |
| 4,369,219 | 1/1983 | Goepp et al. . |
| 4,381,771 | 5/1983 | Gabbay . |
| 4,401,534 | 8/1983 | Goepp et al. . |
| 4,427,477 | 1/1984 | Milgrom . |
| 4,526,578 | 7/1985 | Wong . |
| 4,553,972 | 11/1985 | Vickery . |
| 4,589,880 | 5/1986 | Dunn et al. . |
| 4,607,630 | 8/1986 | Spits . |
| 4,630,602 * | 12/1986 | Strickman et al. . |
| 4,631,060 | 12/1986 | Place . |
| 4,640,272 | 2/1987 | Monett . |
| 4,648,867 | 3/1987 | Conner et al. . |
| 4,693,705 | 9/1987 | Gero . |
| 4,711,235 | 12/1987 | Willis . |
| 4,785,804 | 11/1988 | Tlapek et al. . |
| 4,795,422 | 1/1989 | Conner et al. . |
| 4,822,616 | 4/1989 | Zimmermann et al. . |
| 4,848,363 | 7/1989 | Cattanach . |
| 4,858,624 | 8/1989 | Shihata . |
| 4,883,071 | 11/1989 | Pickhard et al. . |
| 4,895,170 | 1/1990 | Tlapek et al. . |
| 4,923,440 | 5/1990 | Genaro . |
| 4,959,216 | 9/1990 | Daunter . |
| 4,961,436 | 10/1990 | Koch . |
| 5,002,540 | 3/1991 | Brodman et al. . |
| 5,044,376 | 9/1991 | Shields . |
| 5,207,232 | 5/1993 | Shihata . |
| 5,228,456 | 7/1993 | Karg et al. . |
| 5,231,992 | 8/1993 | Leon . |
| 5,398,698 | 3/1995 | Hiller et al. . |

* cited by examiner

INTRAVAGINAL DRUG DELIVERY SYSTEM AND DISCHARGE COLLECTION DEVICE

This is a continuation-in-part of U.S. patent application Ser. No. 08/215,062 ("the '062 application"), filed Mar. 21, 1994, now pending, the entire disclosure of which is incorporated herein by reference. The '062 application is a divisional of U.S. patent application Ser. No. 07/904,367 ("the '367 application"), filed Jun. 26, 1992. The '367 application issued as U.S. Pat. No. 5,295,984 on Mar. 22, 1994. The '367 application was a continuation-in-part of U.S. patent application Ser. No. 07/817,498, filed Jan. 7, 1992, now abandoned, which was a divisional of U.S. patent application Ser. No. 07/446,553 ("the '553 application"), filed Dec. 7, 1989, now abandoned, the entire disclosure of which is incorporated herein by reference. The '367 application was also a continuation-in-part of U.S. patent application Ser. No. 07/865,746, filed Apr. 10, 1992, now abandoned, which was a continuation of the '553 application. The '367 application was also a continuation-in-part of abandoned U.S. patent application Ser. No. 07/852,265, filed Jun. 8, 1992 (based on International Patent Application Number PCT/US90/07159, filed Dec. 7, 1990), the entire disclosure of which is incorporated herein by reference.

BACKGROUND

The present invention relates to a system for intravaginal delivery of drugs and other substances, including but not limited to spermicides, germicides, virucides, medicants, anti-infection agents, hormones, deodorizing materials, lubricants, steroids, anti-bacterial agents, and other pharmacological agents, chemical, natural, or homeopathic agents, and anesthetics. The invention also relates to an improved device for reliably, comfortably and conveniently introducing drugs and/or other substances into the vagina.

The prior art has failed to provide a satisfactory system for delivering drugs and other substances to the vagina. Among other things, the prior art has failed to provide an effective intravaginal drug delivery device that can be economically mass produced, easily handled, and worn comfortably within the vagina. Although a number of contraceptive devices have been designed to deliver spermicidal substances and other active agents, such prior art devices are all unsatisfactory, for a variety of reasons.

U.S. Pat. No. 4,785,804 (Tlapek), for example, refers to a disposable cervical cap which is pre-treated with nonoxvl-9 or other spermicides. The Tlapek device has a thin flexible dome and an integral rim. The rim has an inwardly directed annular groove for gripping the cervix wall to keep the cap in position. In the Tlapek device, the dome and the rim provide a contraceptive barrier, and the spermicide is used to increase the contraceptive effect. An integrally molded loop is provided to remove the cervical cap. According to Tlapek, a string, ring or tab could also be used to remove the device from the vagina. The Tlapek cap is unsatisfactory because among other things it requires a removal device which increases its complexity and cost of manufacture. In addition, the Tlapek device may be difficult to locate and remove from its installed position gripping the cervix, and the manner in which its annular groove is located snugly over the cervix may cause discomfort in some users.

U.S. Pat. No. 4,526,578 (Wong) discloses another disposable device for delivering spermicide. The Wong device is in the form of a dome-shaped occlusive diaphragm that fits snugly within the vagina, covering the cervix and part of the anterior vaginal wall. The prior art Wong diaphragm has an annular reservoir formed of porous material. Spermicide is located within the porous reservoir. A film structure is integrally formed with the annular reservoir. According to Wong, the film structure may also incorporate spermicide. The active spermicidal agent may be added to the film structure during its formation.

The Wong device has several disadvantages. First, its annular reservoir would be complex and difficult to produce economically. Moreover, the diaphragm-shaped device would be difficult to collapse and insert by hand into the vagina. The annular reservoir has a circular cross-section and consequently would tend to twist if diametrically opposite portions were pinched toward each other. Moreover, the reservoir would tend to slip out from between the user's fingertips. Another problem with the Wong device is that its film material could not be relied upon to fold into a narrow, low-profile configuration for convenient, comfortable insertion. Moreover, the snug internal fit for which the Wong device is designed could cause discomfort with some users.

U.S. Pat. No. 5,044,376 (Shields) discloses a contraceptive diaphragm. The device has a tensioning spring and a receptacle for receiving a foam pad. The pad contains spermicide that is released by diffusion into the vagina. A retaining ring is provided for holding the pad in place. The pad and the retaining ring add complexity to the Shields device and would make it relatively difficult to manufacture. Another disadvantage of the Shields device is that it would not be easily compressible into a low profile configuration for insertion. In particular, the device could not be compressed into a figure-eight-shaped configuration with the pad substantially located within the spring. Moreover, the Shields device is generally bulky and does not appear to have been designed for comfort. Shields also discloses a drug delivery device in the form of a cervical cap.

U.S. Pat. No. 4,822,616 (Zimmermann) discloses a vaginal ring for time-released introduction of steroid hormones. The Zimmermann ring is formed of injection molded silicone elastomer. The cross-section of the ring is kidney-shaped. The Zimmermann ring is formed in several layers. This complex, multi-layer construction would make it relatively difficult and expensive to manufacture. Moreover, the ring's flat profile would be difficult to handle. The height of the ring is less than its thickness. Therefore, it would be relatively difficult to compress the ring into a figure-eight-shaped position for insertion. The ring would tend to twist and slip out from between the user's fingers. Another disadvantage of the Zimmermann ring is that it does not appear to have been designed for comfort. Moreover, the prior art ring has no film covering its central open space. Consequently, the Zimmermann device has reduced surface area available for delivering drugs or any other substances, and the Zimmermann device could not be used to collect or contain fluid.

Other prior art systems for delivering substances into the vagina are shown by U.S. Pat. No. 4,630,602 (Strickman), U.S. Pat. No. 4,589,880 (Dunn), U.S. Pat. No. 4,553,972 (Vickery), U.S. Pat. No. 4,311,543 (Strickman '543), U.S. Pat. No. 4,286,587 (Wong '587), U.S. Pat. No. 4,219,016 (Drobish), U.S. Pat. No. 4,198,976 (Drobish '976), U.S. Pat. No. 3,854,480 (Zaffaroni), and British Patents Nos. 260,600 (Fiessler) and 21,588 (Fickert).

SUMMARY

The present invention alleviates to a great extent the disadvantages of the known substance delivery devices by providing a device which is easily compressible to a low profile insertion configuration, and which has a rim whose height is greater than its thickness, and which is arranged to provide an elastomeric outward holding force to hold it in position.

The invention may be used to deliver drugs and/or other agents topically and/or systematically through vaginal mucosa. The invention may also be used to effect intravaginal drug delivery of time released and non-time released medicants for all diseases of the vagina and other reproductive organs and any and all diseases of the entire female anatomy. The invention may be used by both menstruating and non-menstruating females. For example, for the treatment of yeast and fungal infection, medication can be delivered without interruption during menstruation. Additionally, the invention may be used for intravaginal delivery of hormones for birth control and for treatment of the female anatomy, such as during menopause.

The invention may also be used for the delivery of time released and non-time released deodorizing materials for odor prevention, for the delivery of lubrication, and for the delivery of steroids, anti-bacterial agents or any pharmacological agent, chemical, natural, or homeopathic agents. Moreover, the invention may be used for intravaginal delivery of anesthetic for local surgical procedures and for general surgical procedures and for the delivery of pain relieving medication for intermittent and chronic pain, as well as for drug delivery for pregnant women for any and all prophylaxis and illnesses particular to the fetus and/or mother-to-be.

Moreover, the present invention may be used to provide a safe sex barrier, in particular as a barrier during sexual contact to aid in the prevention of the transmission of diseases. The effectiveness of the invention in this regard may be enhanced by using a device with, or for the delivery of, non-oxynol 9 or other specific medicants.

The invention may also be used for the delivery of drugs and other substances in veterinary applications including primates other than humans and other animals.

Moreover, the invention may be employed as an aid to conception for humans, primates, and other animals. Conception can be aided by either using a collector for retaining sperm in the vaginal vault after intercourse or by placing sperm in or on a delivery device and then inserting it in the vaginal vault. This is different from and not a substitute for the medical procedures of artificial insemination that are required in certain circumstances and that are done by doctors in a clinical/hospital setting.

In one aspect of the invention, a drug delivery device is provided with a rim which has a generally rectangular cross-section and which is readily compressible into a narrow, figure-eight-shaped configuration with reduced tendency to twist or slip from between the user's fingers.

In another aspect of the invention, a flexible film is attached to the rim. The film may be used to provide surface area for drug delivery. The film may also be used to close off the device to collect fluid such as menstrual discharge. The film is preferably collapsible so as to be substantially enclosed within the rim to provide a low profile during insertion and when the device is located within the vaginal canal.

In another, separate aspect of the invention, the rim and the film may be arranged such that compressing diametrically opposed portions of the rim toward each other causes a leading portion of the rim to dip downwardly to facilitate proper insertion of the device under the cervix.

In another aspect of the present invention, the dimensions and materials of the device, including the dimensions and materials of the rim, are selected so as to optimize the device's convenience, comfort and reliability. The structure of the present invention may be sized for comfort during wearing while still being held in position by compression of the vaginal wall on the rim. The comfort is achieved in part by a rim that becomes softened or relaxed somewhat at body temperature. In a preferred embodiment of the invention, the reservoir also becomes softened at body temperature, which enhances the device's comfort.

In a preferred embodiment of the invention, a single size device may be adequate for use for a range of sizes of vaginal canals. Even when the device is used to collect menstrual fluid, a tight fit may not be needed to inhibit the passage of menstrual fluid around the rim.

Another advantage of the present invention is that, because it may be made of a material that is chemically inert and non-toxic, it should not be prone to health problems that other products with absorbent materials seem to cause. Moreover, the material of the present invention may allow for adjustment to individual shapes and afford excellent comfort while maintaining its original form. The present invention may be constructed of latex, polymers, and/or elastomers.

The present invention also relates to an intravaginal substance delivery system that has no fibrous absorbent material. The present invention also relates to an intravaginal substance delivery system that has no absorbent material.

The present invention also relates to a discharge collection device that is convenient to use, comfortable to wear, and reliable. The present invention may be used to seal off the blood environment to inhibit the growth of bacteria and entry of air and thus hinder the odor which results from the oxidation and decomposition of menstrual flow.

The present invention also relates to a specimen collector to collect blood and/or vaginal, cervical and/or uterine discharge.

Another object of the invention is to provide a device for vaginal discharge collection and/or intravaginal substance delivery, with the device being designed for economical mass production, such that the device can be conveniently disposed of after a single use.

It is yet a further object of the present invention to provide a discharge collector with any of the foregoing advantages and which provides time released and non-time released dosages of substances for both menstruating and non-menstruating females so that there will be substantially no interruption of treatment, which substance may be, for example, medication, lubrication, deodorants, hormones and analgesics.

It is another object of the present invention to provide a drug delivery device which does not require individual fitting for each user and which may be produced economically enough to be used as a disposable product.

It is yet another object of the present invention to provide a drug delivery device which is easy to insert and remove without scraping delicate tissue.

It is still another object of the present invention to provide a drug delivery device which also provides a barrier against the blood environment.

It is a further object of the present invention to provide a drug delivery device which is light weight without the bulk associated with other devices and which once inserted cannot be felt by the user so that the user is free of the annoying awareness associated with other devices.

It is another object of the present invention to provide a discharge collector with any of the foregoing advantages and which is inexpensive and therefore available to all women.

Other objects and advantages of the present invention will become apparent from the following detailed description and drawings which illustrate preferred embodiments of the present invention.

DETAILED DESCRIPTION OF PREFERRED EMBODIMENTS

Figure 1:
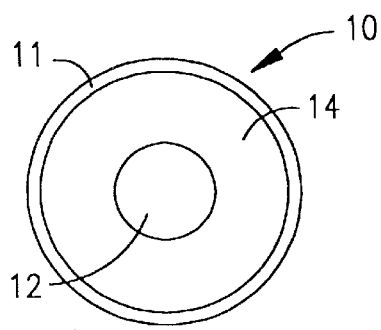
FIG. 1 is a top view of a first preferred embodiment of a discharge collector according to the present invention.
Figure 2:
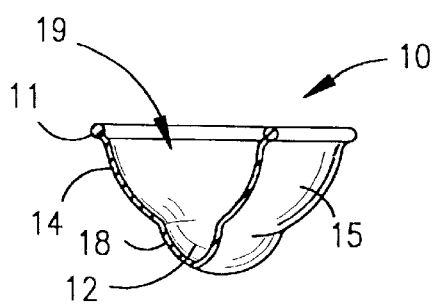
FIG. 2 is a partial cut-away side view of the collector of FIG. 1.

A discharge collector 10 constructed in accordance with one aspect of the present invention is shown in FIGS. 1 and 2. The collector 10 includes a resilient circular rim 11. The body 14 of the collector 10 includes a cup-shaped membrane wall 15 extending downward from the rim and terminating in a reservoir 12 to form a collection space 19. The membrane wall 15 includes at its bottom a reservoir 12 that is a bubble-like protrusion extending at edge 18 from the body 14 surface defined by the membrane wall 15.

The collector 10 is composed of a latex rubber and may be formed by a latex dipping process in which a mandrel is dipped into a tank of coagulating agent, and then dipped into a tank of liquid rubber latex which coagulates on the mandrel. It is then subjected to drying and curing with heat and the device is removed from the mandrel. The material of the preferred embodiment is elastomeric, such as a latex rubber and similar materials. Materials for the collector may be chosen which may be impregnated with a substance to be delivered during use of the device. Such materials are generally known, such as described in U.S. Pat. No. 4,589, 880. Other suitable methods of making the collector may be used, such as by molding.

The rim 11 of the collector 10 is formed entirely of solid latex rubber. However, as discussed below with reference to other preferred embodiments, alternative rim constructions may be used. The diameter of the rim is preferably about two to about four inches (about five to about ten centimeters). The thickness of the rim is preferably less than about one quarter inch (about six millimeters) to result in the greatest degree of comfort to the user. The thickness of the wall, which is substantially impervious to liquid, of the body 14 and the reservoir 12 is preferably more than about one ten thousandth of an inch (about two microns).

The depth of the collector 10 from the rim 11 to the bottom of the reservoir 12 is preferably about one to three inches (about two to eight centimeters). The depth of the reservoir 12 from the edge 18 to the bottom of the reservoir 12 is preferably about one sixteenth to one half of an inch (about two millimeters to about thirteen millimeters). The volume of the collection space 19 is preferably about one to about two ounces (about fifteen to about thirty milliliters).

Figure 9:
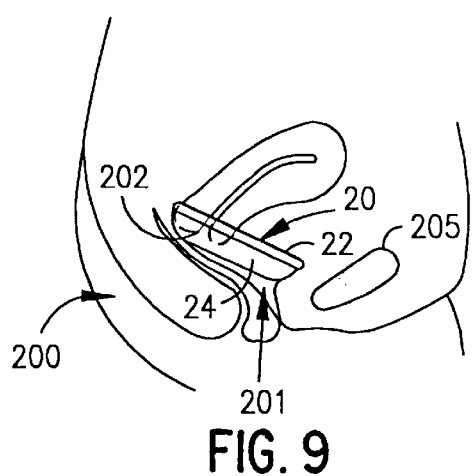
FIG. 9 is a view of the collector of FIG. 3 in place in the vaginal canal.

The thickness and diameter of the rim will depend upon the stiffness of the material used as the rim should be resilient and flexible to be inserted into position and to exert sufficient force to hold the collector 10 in position during use as discussed further below in reference to FIG. 9. The thickness of the body 14 will depend upon the properties of the material used so that the body 14 will have sufficient strength and flexibility.

Figure 3:
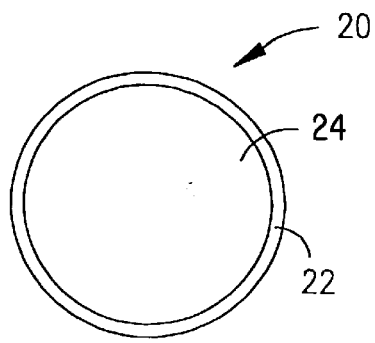
FIG. 3 is a top view of a second preferred embodiment of a discharge collector according to the present invention.
Figure 4:
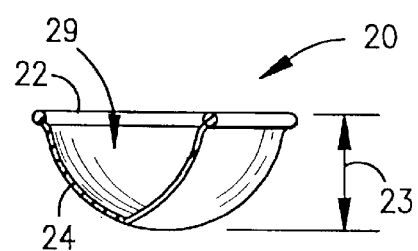
FIG. 4 is a partial cut-away side view of the collector of FIG. 3.

Refer to FIGS. 3 and 4, there being shown a second preferred embodiment of a discharge collector, generally designated by reference numeral 20, according to the present invention. The collector 20 includes a resilient circular rim 22. The body 24 of the collector 20 is an impervious cup-shaped membrane wall extending downward from the rim 22 to form a collection space 29. The construction of the collector 20 is essentially the same as the collector 10, but the collector 20 does not include the reservoir feature. The device 20 may be used to collect discharge, including uterine, cervical, vaginal and/or mucosal discharge, and including blood and tissue sloughed off from a woman's uterus during menstruation.

In operation, the device 20 is inserted into the woman's vaginal canal 201 (FIG. 9) such that portions of the rim 22 are located behind the cervix 202 and behind the pubic bone 205. In this position, the resilient rim 22 exerts a resilient, radially outward force on the wall of the vaginal canal 201. The rim 22 also contacts and exerts a force against the wall of the vaginal canal 201 at points around the periphery of the rim 22, which force is sufficient to effectively prevent menses or other discharge from passing between the rim 22 and the vaginal canal wall 201. The resilient outward force of the rim 22 is sufficient to maintain the device 20 in its illustrated position.

The outward force of the resilient rim 22 is also sufficient to effectively prevent discharge from passing between the rim 22 and the wall of the vaginal canal 201. Therefore, discharge from the cervix 202 is collected within the cup-shaped body 24. After a period of time, the device 20 is removed from the vaginal canal 201, and disposed of along with the collected discharge. A new device 20 is then inserted into the position illustrated in FIG. 9.

The amount of discharge that can be collected within the body 24 is a function of the device's depth 23 (FIG. 4). Increasing the depth 23 increases the amount of discharge that can be collected within the device 20, and therefore increases the amount of time that the device 20 can be used. An increased depth 23 also makes it easy to remove the device 20, as explained in more detail below. However, the depth 23 cannot be so great as to cause discomfort or make it difficult to insert the device 20 into the vaginal canal 201. Generally, the depth 23 of the device 20 measured from the top of the rim 22 to the bottom of the body 24 is at least about one and one-half centimeters and no more than about eight centimeters. A preferred range for the depth 23 is about four to about six centimeters.

The cross-sectional thickness of the round rim 22 will depend upon the stiffness of the material used. The rim 22 should be flexible enough to be easily and reliably inserted into position, and yet stiff enough to exert sufficiently radially outward force to hold the device 20 in position and to adequately prevent discharge from leaking around the rim 22, i.e., between the rim 22 and the wall of the vaginal canal 201. In the illustrated embodiment, the round rim 22 is formed entirely of an appropriately stiff elastomer, with a thickness of about six millimeters.

The wall of the cup-shaped body 24 should be thick enough to provide the desired strength, flexibility, durability and fluid imperviousness. In the illustrated embodiment, the body 24 is formed of latex rubber and is about two mils thick.

The device 20 may be formed by a latex dipping process involving the following steps: dipping a mandrel into a tank of coagulating agent; then dipping the mandrel into a tank of liquid rubber latex which coagulates on the mandrel; drying and curing the coagulated rubber latex; and removing the cured device from the mandrel. Other suitable methods of making the device 20, such as molding, may be used.

Figure 5:
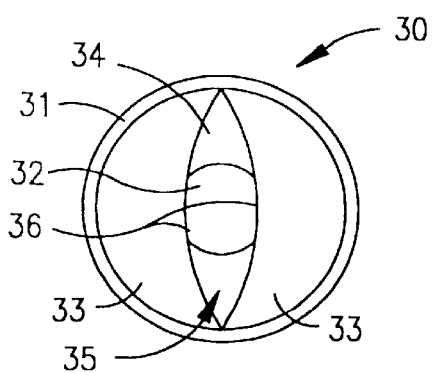
FIG. 5 is a top view of a third preferred embodiment of a discharge collector according to the present invention.
Figure 6:
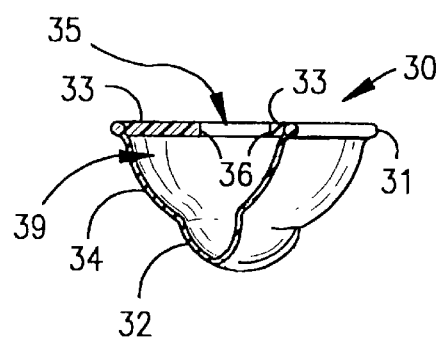
FIG. 6 is a partial cut-away side view of the collector of FIG. 5.

FIGS. 5 and 6 show a third preferred embodiment of a vaginal discharge collector, generally designated by reference numeral 30, according to the present invention. The collector 30 includes a resilient circular rim 31. The body 34 of the collector 30 is a cup-shaped membrane wall extending downward from the rim to form a collection space 39. The membrane wall includes at its bottom a reservoir 32 that is a bubble-like protrusion on the body 34 surface defined by the membrane.

The collector 30 includes a closure means in the form of two membranes 33 to inhibit menses or other vaginal discharge from exiting the collection space 39. Membrane 33 extends across the circular area defined by the rim 31 forming, between their edges 36, a slit 35 which extends across the diameter of the rim 31. The edges 36 are curved so that the width of slit 35 is greatest at the center and the edges 36 come together at the rim 31. The area of the slit 35 is preferably between about five percent and about ninety five percent of the area defined by the rim 31. The sizes of the slit 35 and the membrane 33 are chosen such that the slit 35 is large enough for fluid to enter the collector 30 and the membranes 33 inhibit the exit of fluid to the desired extent. The thickness of the membranes 33 is preferably greater than about one ten thousandth of an inch (about two microns). The membranes 33 may be used for drug delivery, and the size and thickness of the membranes 33 may be chosen to meet the dosage needs.

Figure 7:
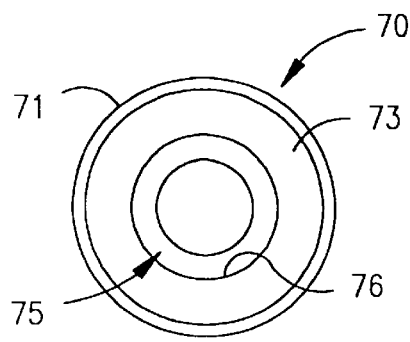
FIG. 7 is a top view of a fourth preferred embodiment of a discharge collector according to the present invention.
Figure 8:
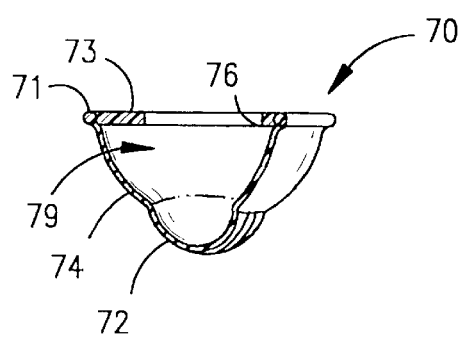
FIG. 8 is a partial cut-away side view of the collector of FIG. 7.

Refer now to FIGS. 7 and 8, there being shown a fourth preferred embodiment of a discharge collector, generally designated by reference numeral 70, according to the present invention. In FIG. 7, a top view of the collector 70 is shown. The collector 70 includes a resilient circular rim 71. The body 74 of the collector 70 is a cup-shaped membrane wall extending downward from the rim to form a collection space 79. The membrane wall includes at its bottom a reservoir 72 that is a bubble-like protrusion on the body 74 surface defined by the membrane.

The collector 70 includes a closure means in the form of a membrane 73 to inhibit the exit of menses or other discharge from exiting the collection space 79. The membrane 73 extends around the periphery of the circular area defined by the rim 71 forming with its edge 76 a circular opening 75. The width of the membrane 73 between edges 76 and rim 71 is preferably about five percent to about ninety five percent of the diameter of the rim 71.

Figure 10:
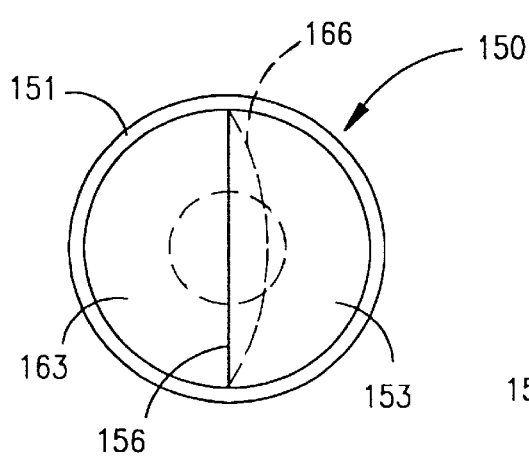
FIG. 10 is a top view of a fifth preferred embodiment of a discharge collector according to the present invention.
Figure 11:
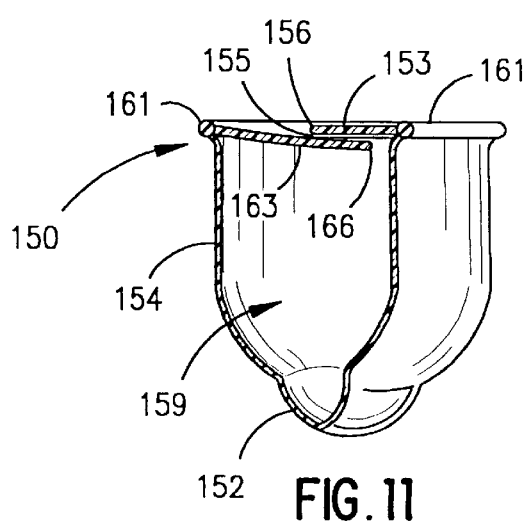
FIG. 11 is a partial cut-away side view of the collector of FIG. 10.

Refer now to FIGS. 10 and 11, there being shown a fifth preferred embodiment of a discharge collector, generally designated by reference numeral 150, according to the present invention. In FIG. 10, a top view of the collector 150 is shown. The collector 150 includes a resilient circular rim 151. The body 154 of the collector 150 is a cup-shaped membrane wall extending downward from the rim to form a collection space 159. The membrane wall includes at its bottom a reservoir 152 that is a bubble-like protrusion on the body 154 surface defined by the membrane.

Note that the body 154 is deeper, preferably about three to about four inches (about eight to about ten centimeters) in depth, and has a larger capacity, preferably about two to four ounces (about thirty to sixty milliliters), than the collector 10 of FIGS. 1 and 2. This embodiment is particularly useful for over-night use or when relatively large volumes of discharge are to be collected.

The collector 150 includes a closure means that includes two membranes 153 and 163. The upper membrane 153 extends over approximately half of the area defined by the rim 151 and has no or relatively little slack so that it extends approximately horizontally. The lower membrane 163 extends over more than half of the area defined by the rim 151. The edge 166 of the membrane 163 extends underneath the upper membrane 153. The slit 155 formed between the edge 156 of the membrane 153 and the edge 166 of the membrane 163 allows discharge to drain into the collection space 159. However, as collected fluid moves upward towards exiting the device, force is exerted upward on the membrane 163 to cause it to contact the underside of membrane 153. In this manner, the closure means shuts the slit 155 to inhibit the exit of fluid from the collection space 159.

All of the collectors illustrated in FIGS. 1 through 11 may be formed of the same latex rubber material. However, the materials and the size and thickness of the various components of the invention should be chosen for the considerations discussed with respect to one or more of the preferred embodiments. These conditions may be applicable to each of the preferred embodiments described above, as well as other embodiments of the present invention, even though not individually stated for each embodiment in conjunction with its description above. Also, various features of the illustrated devices may be used with other devices. The present invention is not limited to the embodiments illustrated and described in detail herein.

The collectors shown in FIGS. 1–11 may be used to deliver drugs and other substances into the vagina, and the collectors may be used exclusively for substance delivery. In other words, the devices may be used for both purposes or they may be used solely for substance delivery. With respect to use of the illustrated collectors for the delivery of drugs and other substances, the substances may be applied to the collectors in a number of ways. The substance, which may be a therapeutic agent, may be applied to a collector by mixing the substance or its precursors with the material of the collector's body, rim, reservoir, membrane, and/or other portion during manufacturing, such as prior to forming the collector during a molding operation by mixing the substance with the ingredients, whether dry or liquid, to be molded. Another way to apply the substance is to inject, impregnate, or absorb it partially or completely through the material (or cavities or porous portions thereof) of the collector's body, rim, film reservoir, and/or other portions after such portions have been formed. Yet another way to apply the substance is to coat portions of the collector surface with the substance.

Figure 12:
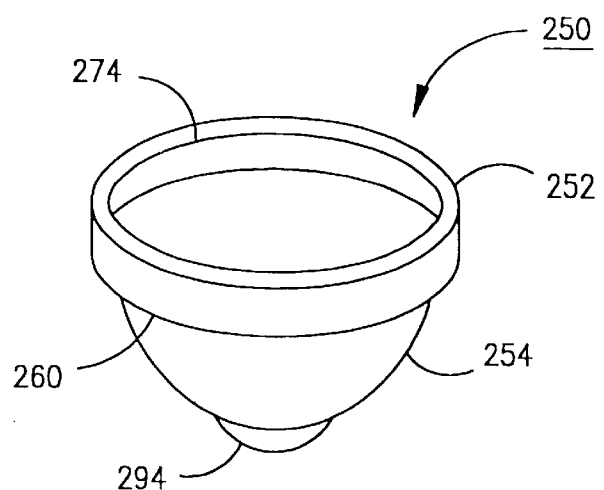
FIG. 12 is a perspective view of a discharge collection device according to another preferred embodiment of the present invention.
Figure 13:
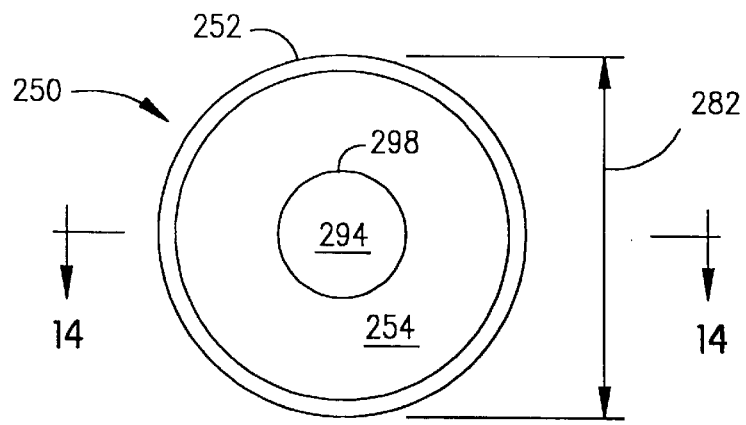
FIG. 13 is a top view of the discharge collection device of FIG. 12.
Figure 14:
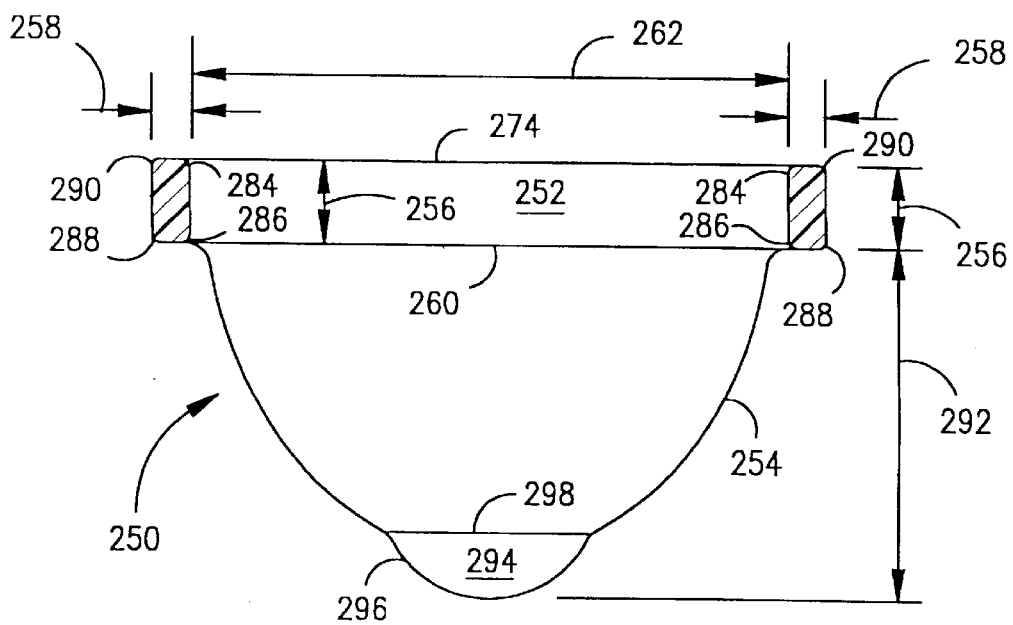
FIG. 14 is a cross-sectional view taken along the line 14—14 of FIG. 13.

Refer now to FIGS. 12 and 13, there being shown a device 250 constructed in accordance with another, presently preferred embodiment of the present invention. The device 250 may be used to collect fluid or it may be used to deliver substances into the vagina or it may be used for both purposes. The device 250 is formed of a thick elastomeric rim 252 and a highly flexible film or reservoir 254. The reservoir 254 is formed of a thin, impervious, elastomeric film material and is sealingly connected to the rim 252. As illustrated in FIG. 14, the rim 252 has a rectangular cross section (with substantially parallel inner and outer sides, and with rounded edges), with its height 256 being substantially greater than its thickness 258.

The amount of discharge typically generated during a menstrual cycle is two to eight tablespoons (thirty to one hundred twenty milliliters). The exemplary devices 250, 10, 20, etc. illustrated in this application are designed to be worn internally for about four hours. During this four hour time period, a woman typically discharges about one teaspoon (five milliliters) of menstrual fluid, although much larger volumes of liquid may be discharged during heavy flow periods.

Figure 15:
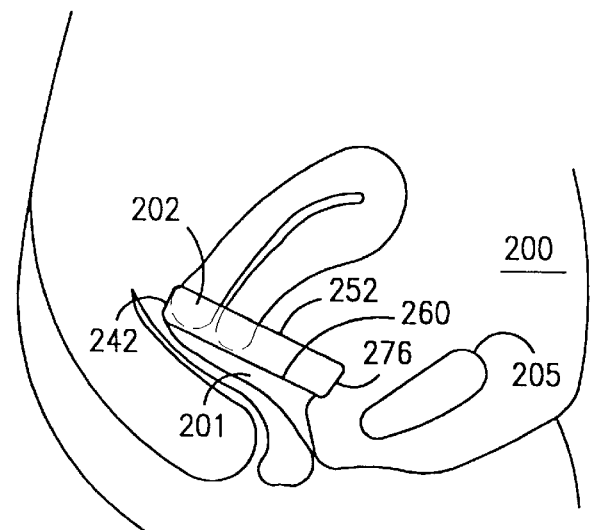
FIG. 15 is a side view of the collection device of FIG. 12 in place within the vaginal canal.

In operation, the device 250 is inserted into the woman's vaginal canal 201 (FIG. 15) such that portions of the rectangular rim 252 are located behind the cervix 202 and behind the pubic bone 205. In this position, the rim 252 is slightly compressed and therefore exerts an elastomeric, radially outwardly directed force on the wall of the vaginal canal 201. This force maintains the device 250 in its illustrated position during use, and prevents discharge from escaping between the rim 252 and the wall of the vaginal canal 201.

The reservoir 254 can be extended to assume a cup-shaped configuration, as illustrated in FIGS. 12 and 13. However, when the device 250 is in its collection position within the vaginal canal 201 (FIG. 15), the reservoir 254 is collapsed inwardly toward the cervix 202 by the walls of the vaginal canal 201. In this position, i.e., while discharge from the cervix 202 is being collected within the device 250, the reservoir 254 remains in its collapsed configuration essentially coplanar with the bottom edge 260 of the rim 252. Thus, in FIG. 15, the reservoir 254 is essentially hidden from view behind the rim's bottom edge 260.

Discharge (such as vaginal and/or cervical discharge) is collected within a generally cylindrical space defined within the rim 252. This collection space is a virtual space in the sense that the rim 252 separates the walls of the vagina 201 to create a collection space where there is no space otherwise. In the illustrated embodiment of the invention, the inner diameter 262 of the rim 252 is approximately sixty two millimeters, and the collection volume is approximately thirty milliliters. The volume of this collection space is approximately equal to the height 256 of the rim 252 times the area surrounded by the rim 252. The reservoir 254 does not contribute significantly to the volume of the collection space, except that folds within the reservoir 254 may provide a trickling down effect, as explained below. While the device 250 is collecting discharge, the primary function of the reservoir 254 is only to seal off the bottom of the device 250. The ability of the reservoir 254 to assume a collapsed configuration allows the device 250 to be inserted and worn internally with greater comfort. Another advantage of the collapsed configuration is that it provides additional surface area for substance delivery purposes.

Figure 16:
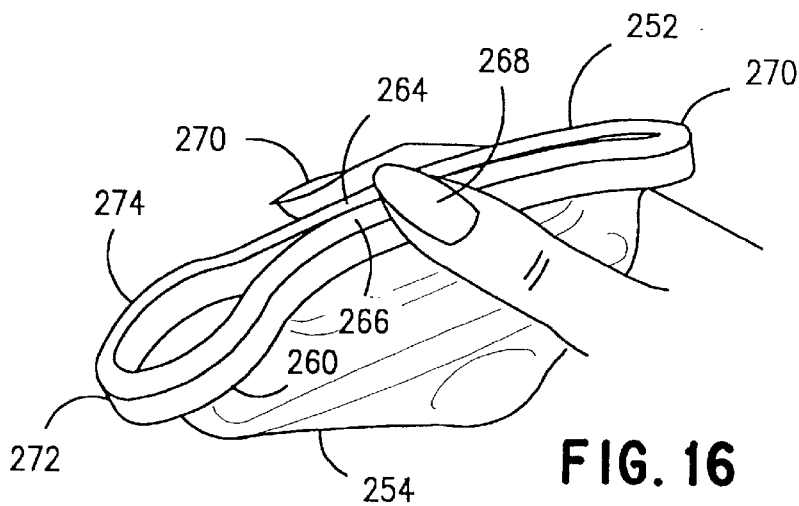
FIGS. 16, 17 and 18 are a perspective view, a top view and a side view, respectively, of the discharge collection device of FIG. 12, in a compressed configuration ready for insertion.
Figure 17:
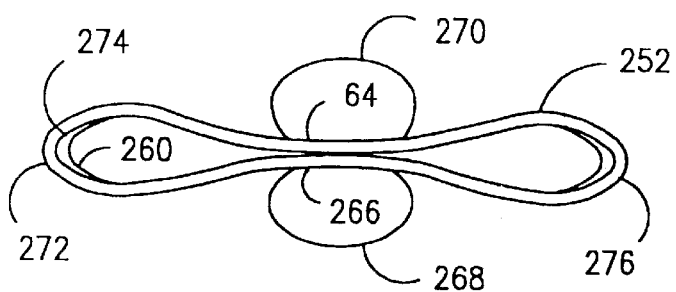

To insert the device 250 into the vaginal canal 201 adjacent the cervix 202, diametrically opposed portions 264, 266 (FIGS. 16 and 17) of the rim 252 are pressed into contact with each other between two of the user's fingers 268, 270 (which may, for example, be the user's thumb 268 and middle finger 270), such that the rim 252 assumes a low profile, figure-eight-shaped configuration. In the low profile configuration, the film reservoir is substantially collapsed within the rim or located adjacent the rim during insertion of the device, which makes it easier and more comfortable to insert the device. As used herein, the term "low profile" configuration means a configuration like that shown in FIG. 17, where the rim 252 is compressed into a narrow figure-eight-shaped configuration with substantially no twisting, and with the film reservoir 254 substantially collapsed within the rim 252 or located adjacent the rim 252 during insertion of the device. The thinness and flexibility of the reservoir 254 contributes to the ability of the device to assume the low profile configuration during insertion.

The compression applied by the fingers 268, 270 is not released (i.e., the portions 264, 266 remain in contact with each other) until a leading portion 272 of the rim 252 is in position behind the cervix 202. The compression applied by the fingers 268, 270 is then released, allowing the rim 252 to elastomerically restore itself to its initial, generally circular configuration, such that the rim 252 applies a gentle, elastomeric, radially outwardly directed force against the wall of the vaginal canal 201.

During insertion, the relatively rigid rim 252 (at room temperature) acts as an applicator for the device 250. During use, the temperature of the rim 252 is increased to body temperature which softens the rim 252 and thereby causes the compressibility of the rim 252 to be reduced substantially. The softening effect provides for a more comfortable fit. The softening effect also makes it easier to remove the device 250. Preferably, the reservoir 254 is made of the same material as the rim 252. The reservoir 254 also softens or relaxes somewhat in response to body temperature, which makes the device 250 more comfortable to use.

Naturally, the opposed portions 264, 266 and the leading and trailing portions 272, 276 of the rim 252 are randomly determined by the user. These portions are not defined until the user grasps the device 250 for insertion. All that is important in this regard is that the portions 264, 266 that come into contact with each other are initially approximately diametrically opposed to each other. The leading and trailing portions 272, 276 will then be defined on opposite sides of the user's fingers 268, 270.

The generally rectangular cross section of the rim 252 (FIG. 14) is very important. If the thick rim 252 had a circular cross section, it would tend to twist when compressed into the figure-eight-shaped insertion configuration, and further twisting could occur during insertion of the device 250 into the vaginal canal 201. Providing the rim 252 with a generally rectangular cross section therefore is very advantageous in terms of reliability and ease of insertion. Significantly, with the rectangular cross section, the device 250 can be inserted without insertion tools. Another advantage of the generally rectangular cross section is that the flat inner surfaces of the opposed portions 264, 266 do not tend to slip past each other when the rim 252 is compressed into the low profile insertion configuration illustrated in FIG. 16. Another advantage of the generally rectangular cross-sectional configuration is that the substantially flat outer surfaces of the rim 252 at the opposed portions 264, 266 can be held stably in contact with the user's fingertips 268, 270. If the rim 252 had a circular cross-sectional configuration, there would be a greater tendency for the opposed portions 264, 266 to slip past each other in the insertion configuration, and the outside surfaces of the rim 252 would be more difficult to handle.

Another advantage of the generally rectangular configuration for the rim 252 is that it provides increased surface area for drug delivery. In particular, the generally rectangular configuration provides more surface area than a circular cross-sectional configuration would provide for the same volume of thermoplastic material. The increased surface area is advantageous regardless of whether the substance to be delivered is impregnated into the material of the rim 252 and/or the substance is applied to the exterior of the rim 252, for example as a gel, cream or foam.

Figure 18:
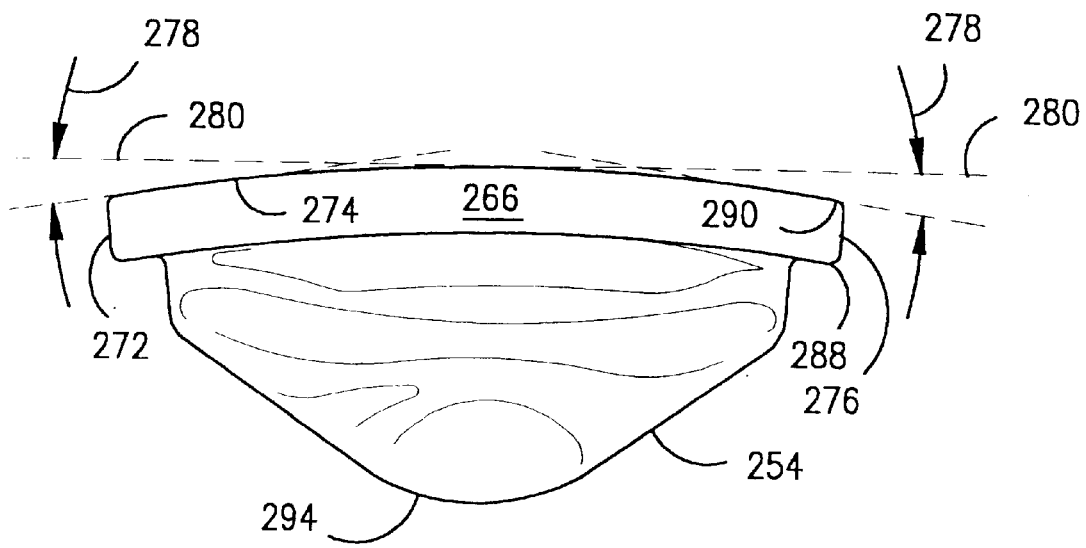

Further, the rim 252 and the reservoir 254 may be arranged such that compressing the rim 252 into its figure-eight-shaped configuration (FIGS. 16, 17 and 18) causes the top edge 274 of the rim 252 to curve slightly downwardly, as illustrated in FIG. 18. The resulting down-dip curvature 278 of the rim's leading portion 272 makes it easier to maneuver the leading portion 272 under the cervix 202 during insertion of the device 250 into the vaginal canal 201. Preferably, the down-dip curvature 278 (i.e., the angular extent to which the leading portion 272 dips downwardly relative to a nominal plane 280 when the rim 252 is in its fully compressed, figure-eight-shaped configuration) is no less than approximately five degrees and no more than approximately fifteen degrees. If the down-dip curvature 278 is too small, some users may have difficulty moving the leading portion 272 underneath the cervix 202 during insertion. If the down-dip curvature 278 is too great, it may be difficult to move the device 250 through the vaginal canal 201.

The device 250 may be removed in a variety of ways. For example, the user may insert her finger into the vaginal canal 201 and grasp a radially inner surface of the rim 252. Preferably, the device 250 is not removed by pulling on the reservoir 254. Since the reservoir 254 is highly flexible, the user's finger can be easily pushed through the plane containing the bottom edge 260 of the rim 252, allowing the user to easily grasp the rim 252. The depth 292 of the reservoir 254 is a significant factor in the removability of the device 250. Increasing the depth 292 makes it easier for the user to insert her finger into proper position for removal of the device 250, i.e., adjacent the inner surface of the rim 252. The device 250 may also be removed by placing the finger over the top edge 274 of the rim 252 and using the finger and the thumb to grasp the rim 252 for removal.

As the device 250 is removed from the vaginal canal 201, the reservoir 254 is automatically extended to its generally cup-shaped configuration (FIG. 14) by the weight of the collected fluid. The ability of the reservoir 254 to extend in this manner minimizes the risk of spilling discharge (such as menstrual fluid discharge) during removal and disposal of the device 250. The depth 292 of the extended reservoir 254, as measured from the bottom edge 260 of the rim 252 should be at least approximately thirty millimeters. If the depth 292 were less than approximately thirty millimeters, there may be significant spillage during removal of the device 250 from the vaginal canal 201. Also, if the depth 292 were less than thirty millimeters, some users would find it difficult to grasp the rim 252 to remove the device 250. When the depth 292 is greater than approximately thirty millimeters, the danger of spillage is substantially avoided. A depth 292 greater than approximately fifty millimeters would waste material. Excellent results are obtained when the depth 292 of the film reservoir 254 is approximately forty millimeters. Further, the device 250 may be provided in different sizes, with different depths 292. For example, the depth 292 may be thirty millimeters for a light flow product, forty millimeters for a medium flow product, and fifty millimeters for a heavy flow product.

The present invention is not limited to the specific removal techniques discussed above.

Further, an increased depth 292 (i.e. a depth 292 greater than thirty millimeters) may provide increased volume for discharge collection through a trickling down effect. In use, the reservoir 254 is collapsed and substantially aligned with the bottom edge 260 of the rim 252. However, there may be folds within the collapsed reservoir 254 that extend downwardly beneath the edge 260, and some discharge may trickle down into such folds. Increasing the depth 292 contributes to this trickle down effect by increasing the number and length of such folds. Increasing the number and lengths of folds within the reservoir 254 may also provide more surface area for drug delivery purposes.

The device 250 has an uncomplicated construction so that it can be inexpensively mass produced and marketed. Therefore, once the device 250 has been removed from the vaginal canal 201, it can be simply thrown away and replaced by a new device 250.

The rim 252 is preferably formed of an inert thermoplastic rubber, preferably a blend of two parts of a styrenic-olefinic block copolymer marketed by Shell Chemical Company under the trademark KRATON® and one part low density polyethylene. This blended material is preferred because it is toxicologically acceptable for internal wear, readily available and economical, and readily processible. The block copolymer is particularly preferred because it has anisotropic flow properties, which means that its molecular chains can be caused to orient during plastic flow to increase stiffness perpendicular to the direction of injection molding. Without the anisotropic flow properties of the preferred material, it would be difficult to achieve the desired stiffness perpendicular to the injection molding direction. The low density polyethylene is advantageous because it increases the stiffness of the blend, improves processibility, and reduces the overall cost of the blended material.

The material of the rim 252 should be stiff enough to maintain its shape and provide the desired elastomeric self-restoring force and yet flexible enough to comfortably adjust to individual shapes. The preferred balance between stiffness and flexibility for the material of the rim 252 is obtained when the material has a Shore A hardness of approximately fifty five to approximately seventy five, preferably sixty to seventy, according to the following test method: ASTM D2240. Another important property of the preferred elastomeric material is its ability to soften and conform to the walls of the vagina as its temperature is increased from room temperature to body temperature.

The self-restoring force of the elastomeric rim 252 must be great enough to ensure that the rim 252 will expand with enough strength to form the desired seal against the wall of the vaginal canal 201, and to ensure that the device 250 will not become inadvertently dislodged. On the other hand, the self-restoring force should not be so great as to make it difficult to insert the device 250. A large self-restoring force would also make it difficult to remove the device 250. Moreover, the self-restoring force should be not be so large as to interfere with the safety and efficacy of the device. The preferred material for the rim 252 exhibits a softening effect upon exposure to the temperatures encountered in the vaginal canal 201. This advantageous property allows the rim 252 to more fully conform to the distinct shape of an individual vaginal vault once inserted. This offers greater comfort during wear as well as added protection against potential leakage during use.

Thus, the rim 252 is designed to be relatively stiff at room temperature so as to be easy to insert. The stiffness of the rim 252 decreases after insertion, as its temperature increases, making the device 250 more comfortable to wear and also easier to remove.

The rim 252 has been found to perform well in terms of self-restoring force when the rim 252 has a "compressed hoop strength" of no less than approximately two hundred and fifty grams and no more than approximately one thousand grams, preferably no less than approximately three hundred grams and no more than approximately eight hundred grams. As used herein, the term "compressed hoop strength" means the force needed to initially maintain the diametrically opposed portions 264, 266 of the elastomeric rim 252 in contact with each other when the rim 252 is in its figure-eight-shaped insertion configuration illustrated in FIGS. 16 and 17, with the rim 252 being at room temperature (approximately twenty three degrees Celsius).

The height 256 of the rim 252 is another important consideration. One way to significantly increase the device's collection volume is to increase the rim height 256. However, the rim 252 must not be too high, or it will cause discomfort. The conflicting goals of increased collection volume and increased comfort are satisfactorily balanced when the height 256 of the rim 252 is no less than approximately five millimeters and no more than about fifteen millimeters. Even better results are obtained when the rim height 256 is no less than approximately nine millimeters and no more than approximately eleven millimeters. Within this range, the rim 252 fits snugly and comfortably behind the pubic bone 205. Excellent results are achieved when the rim height 256 is approximately ten millimeters.

The thickness 258 of the rim 252 relative to the rim's height 256 is another important ergonomic consideration. Determining the most advantageous ratio between the height 256 of the rim's parallel sides to the rim's thickness 258 involves trade-offs between space utilization and the stiffness and self-restoring force of the rim 252. If the height to thickness ratio were too great, the rim 252 would either be too high (and therefore uncomfortable) or too flexible (the elastomeric self-restoring force would be too small) such that the rim 252 would tend to twist during insertion. If the ratio were too small, then the rim 252 would form an inadequately small cylindrical collection space and/or would be too thick and would also tend to twist. The best results are achieved when the rim height 256 divided by the rim thickness 258 is no less than approximately two and no greater than approximately three. The most advantageous height to thickness ratio for the preferred embodiment is two and one-half.

An advantage of the present invention is that the diameter of the device 250 does not have to be sized to fit tightly or tailored to an individual user. In one aspect of the invention, the rim 252 forms a gentle seal within the vagina. Therefore, the device 250 can be economically manufactured in a single size and still be acceptable for most woman. A preferred outside diameter 282 for the device 250 is seventy millimeters, but satisfactory results for the single size device are achieved when the diameter 282 is no less than approximately sixty eight millimeters and no more than approximately seventy two millimeters.

It may be advantageous to manufacture the device 250 in three different sizes: (1) a junior size for teenage girls; (2) an intermediate size for nulliparous women (i.e., those who have not had a child) during the child-bearing years; and (3) a larger size for multiparous women (i.e., those who have had children). Such devices would have outer diameters 282 as follows: (1) junior—sixty to sixty five millimeters; (2) nulliparous women—sixty six to seventy four millimeters; and (3) multiparous women—seventy five to eighty millimeters. If a "one size fits all" device is desired, then the outer diameter 282 should be approximately seventy millimeters.

The rim 252 preferably has rounded edges 284, 286, 288, 290. This helps make it easy to insert the device 250 into position for use without scraping delicate tissues. Providing the rounded edges 284, 286, 288, 290 also helps avoid tissue damage during use of the device 250.

The device 250 can be formed by an injection molding process involving the following steps: injection molding the rim 252; attaching a sheet of thermoplastic elastomer to the rim 252; and vacuum thermoforming the film reservoir 254 from the sheet of elastomeric material. Injection molding processes for manufacturing the device 250 are described in more detail in U.S. Provisional Patent Application Ser. No. 60/021,236, the entire disclosure of which is incorporated herein by reference.

The above-described blended material is well suited to the above-described injection molding process because of its anisotropic flow properties. Also, the rim 252, by virtue of its rectangular cross section, is relatively easy to injection mold. In particular, with the rectangular cross section, the rim 252 can be produced with a faster cycle time. This is because the cross section of the rim 252 is such that the injection molded material will rapidly cool and solidify. A rim with the same height 256 but with a circular cross section would take longer to solidify.

The film reservoir 254 is formed generally as thin as practically possible. Making the reservoir 254 very thin makes the device 250 easier to use and more comfortable to wear. However, if the reservoir 254 were less than about one and one-half mils thick, the reservoir 254 could cause discomfort and could be easily punctured. A preferred thickness for the reservoir 254 is about eleven mils. If the reservoir 254 were more than about fifteen mils thick, it might not properly redeploy (extend to its FIG. 14 position) upon removal of the device 250 from the vaginal canal 201.

Advantageously, the reservoir 254 has a dimple 294. During removal of the device 250, vaginal discharge tends to flow into the dimple 294. In the illustrated embodiment, the dimple 294 will hold about one teaspoon (five milliliters) of discharge (i.e., the amount of menstrual fluid typically discharged during a four hour wear cycle). The relatively steep side walls 296 of the dimple 294 cause the discharge to remain within the dimple 294, beneath the upper edge 298 of the dimple 294. The dimple 294 forms a deep, isolated location within the device 250 during removal. The effect is to increase the extent to which discharge remains at the bottom of the device 250 during removal, reducing the likelihood of spillage.

The dimple 294 also functions as a visual indicator. That is, the upper edge 298 can be easily recognized as a point of reference by the woman removing the device 250, making it easy for the woman to make a comparative determination of the amount of discharge within the device 250. The dimple 294 may also contribute to the trickling down effect by increasing the number of folds within the reservoir 254 and by increasing the volume formed by such folds.

The dimple 250 may also be used to contain drugs or other active agents, including drugs in the form of a gel or foam. Thus, the dimple may be used to visually indicate or confirm that the correct volume of gel, foam or other material has been located within the device 250.

Figure 22:
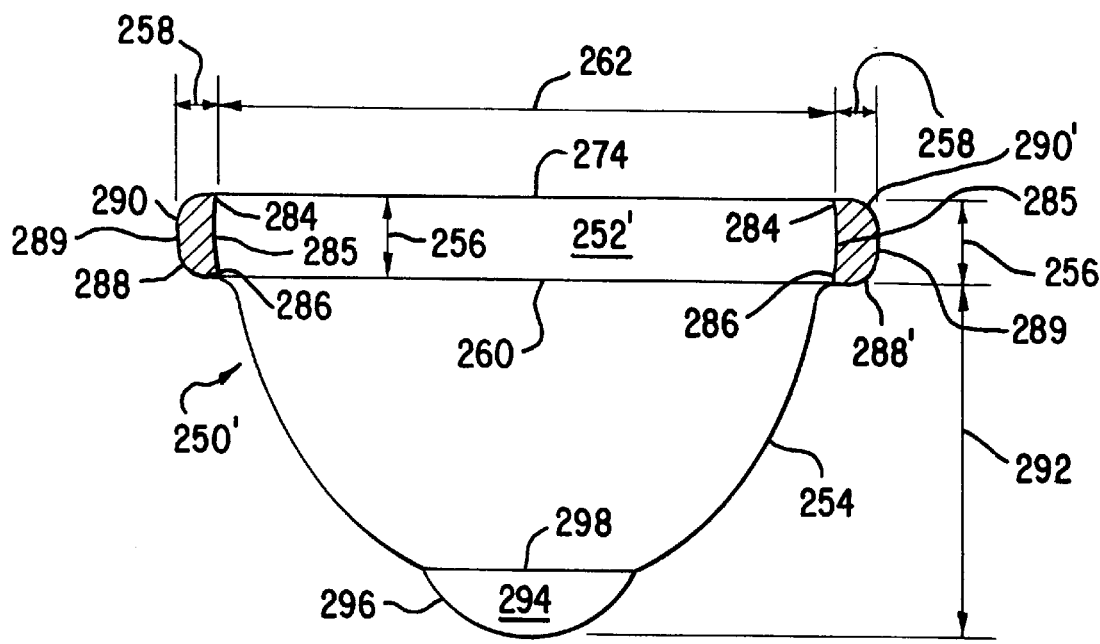
FIG. 22 is a cross-sectional view of a device constructed in accordance with another embodiment of the invention.

A device 250' constructed in accordance with another preferred embodiment of the invention is shown in FIG. 22. To facilitate insertion of the device 250' into position for use, the leading edges 288', 290' of the rim 252' are even more rounded than the inner edges 284, 286. Consequently, the generally rectangular cross-sectional shape of the rim 252' is somewhat D-shaped. In other words, the outer flat surface 289 of the rim 252' (between the edges 288', 290') is shorter than the inner surface 285 (between the edges 284, 286). In addition, the inner surface 285 may be slightly concave. The device 250' of FIG. 22 is otherwise constructed the same as the device 250 of FIG. 14 and may be used in the same ways to obtain the same advantages and benefits as those discussed herein in connection with the device 250 of FIG. 14.

The device 250' shown in FIG. 22 has been used by tens of thousands of women with satisfactory results.

Figure 23:
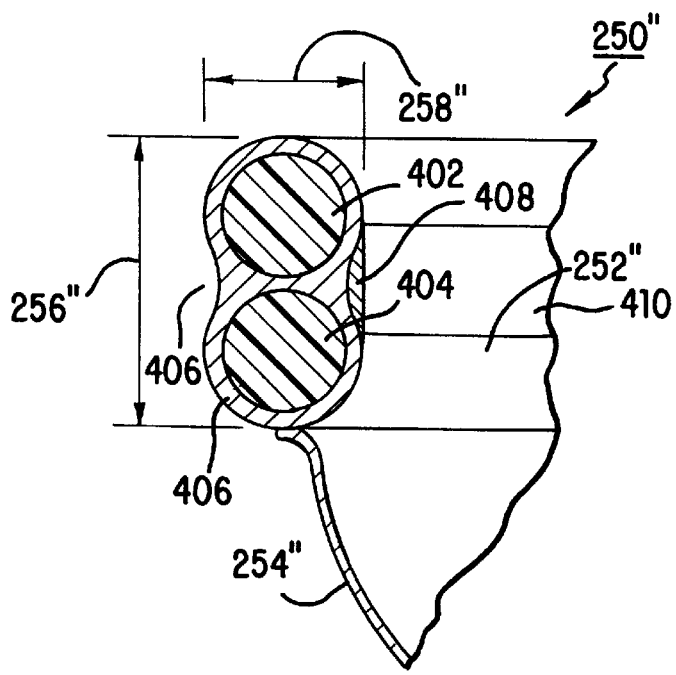
FIG. 23 is a partial cross-sectional view of a device constructed in accordance with another embodiment of the invention.

A device 250" constructed in accordance with yet another embodiment of the present invention is shown in FIG. 23. The device 250" has a rim 252" formed of two rubber O-rings 402, 404 encapsulated in latex rubber 406. The rim 252" may be formed of materials that soften in response to body temperature. The rim 252" may be formed by dipping the O-rings 402, 404 in a liquid solution of latex rubber. The rim 252" has a generally rectangular configuration. The height 256" of the rim 252" is about two and one-half times the rim thickness 258". A latex film reservoir 254" is attached to the bottom of the rim 252" such that the device 250" has an overall configuration like those of the devices 250, 250' shown in FIGS. 14 and 22. The device 250" may be used in the same ways to obtain generally the same advantages and benefits as those discussed herein in connection with the device 250 of FIG. 14.

Although the rim 252" shown in FIG. 22 has a generally figure-eight-shaped cross-sectional configuration, the rim 252" may have other cross-sectional configurations in alternative embodiments. For example, the encapsulating material 406 (surrounding the O-rings 402, 404) may be provided with the D-shaped cross-sectional configuration of the rim 252' shown in FIG. 22. Alternatively, the encapsulating material 406 may be provided with the cross-sectional rim configuration shown in FIG. 14.

Figure 24:
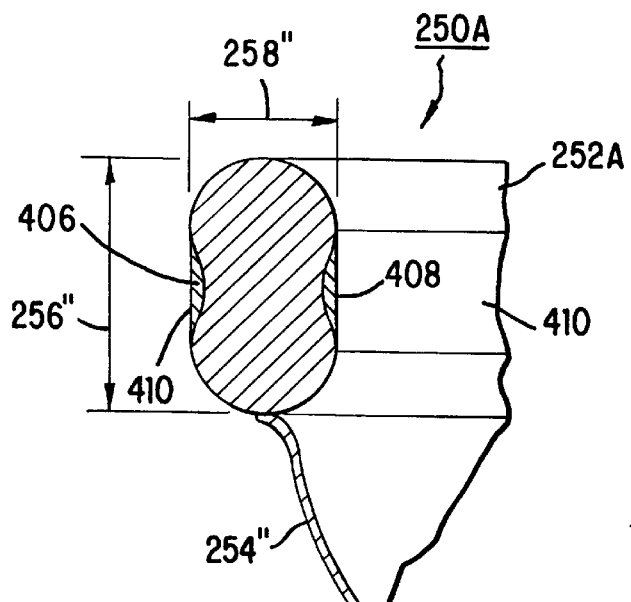
FIG. 24 is a partial cross-sectional view of a device constructed in accordance with yet another embodiment of the invention.

A device 250A constructed in accordance with yet another embodiment of the present invention is shown in FIG. 24. The device 250A has a rim 252A with the same cross sectional configuration as the rim 252" shown in FIG. 23, except that the rim 252 A is formed in one piece without the O-rings 402, 404. The rim 252A may be formed of materials that soften in response to body temperature. The rim 252A has a generally rectangular configuration. The height 256" of the rim 252A is about two and one-half times the rim thickness 258". A latex film reservoir 254" is attached to the bottom of the rim 252A such that the device 250A has an overall configuration like those of the devices 250, 250' shown in FIGS. 14 and 22. The device 250A may be used in the same ways to obtain generally the same advantages and benefits as those discussed herein in connection with the device 250 of FIG. 14.

The annular recesses 406, 408 formed within the cross-sectional configuration of the rims 252", 252A shown in FIGS. 23 and 24 may be used to contain drugs and other substances or medications 410. The substances 410 may be in the form of gels, foams or creams.

Figure 25:
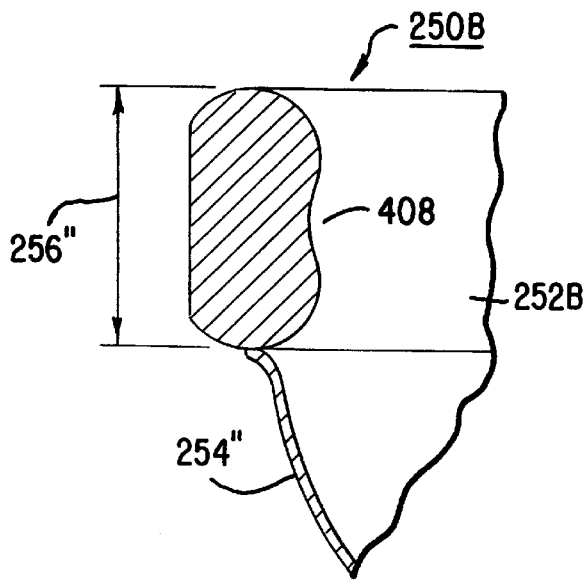
FIG. 25 is a partial cross-sectional view of a device constructed in accordance with yet another embodiment of the invention.

A device 250B constructed in accordance with yet another embodiment of the present invention is shown in FIG. 25. The device 250B has a rim 252B with a B-shaped cross sectional configuration. The rim 252B may be formed of materials that soften in response to body temperature. A latex film reservoir 254" is attached to the bottom of the rim 252B such that the device 250B has an overall configuration like those of the devices 250, 250' shown in FIGS. 14 and 22. The device 250B may be used in the same ways to obtain generally the same advantages and benefits as those discussed herein in connection with the device 250 of FIG. 14.

The inner annular recess 408 of the devices shown in FIGS. 23, 24 and 25 makes the devices easier to handle during insertion. When the opposed portions 264, 266 are compressed toward each other in the manner shown in FIG. 16, the undulating portions of the inner recess 408 engage each other reducing still further the tendency of the rim portions to slip past each other.

Figure 26:
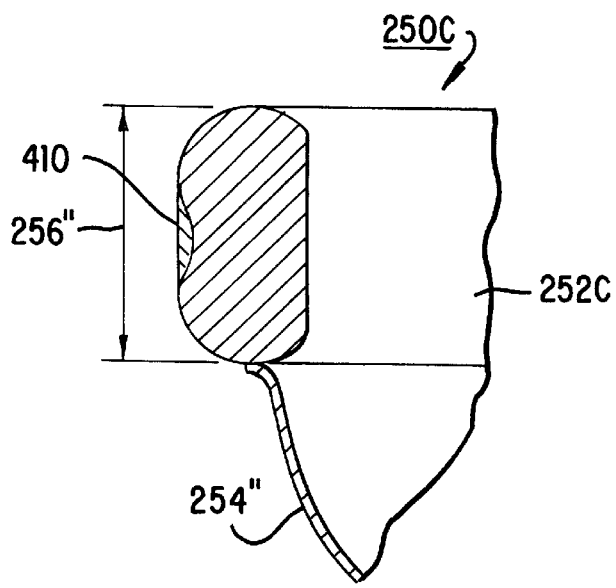
FIG. 26 is a partial cross-sectional view of a device constructed in accordance with yet another embodiment of the invention.

A device 250C constructed in accordance with yet another embodiment of the present invention is shown in FIG. 26. The device 250C has a rim 252C with a reverse B-shaped cross sectional configuration. The rim 252C may be formed of materials that soften in response to body temperature. A latex film reservoir 254" is attached to the bottom of the rim 252C such that the device 250C has an overall configuration like those of the devices 250, 250' shown in FIGS. 14 and 22. The device 250C may be used in the same ways to obtain generally the same advantages and benefits as those discussed herein in connection with the device 250 of FIG. 14. A substance 410 to be delivered intravaginally may be located in the outwardly facing recess of the rim 252C, if desired.

Figure 27:
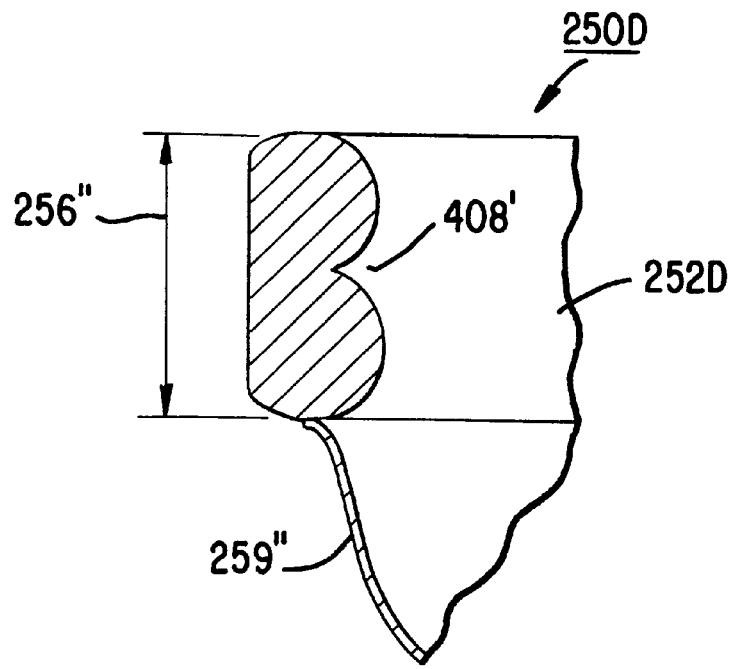
FIG. 27 is a partial cross-sectional view of a device constructed in accordance with yet another embodiment of the invention.
Figure 28:
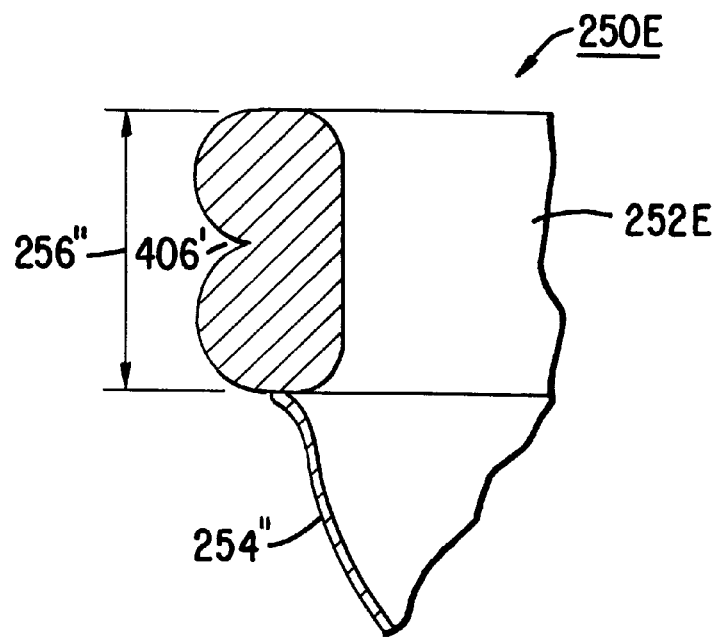
FIG. 28 is a partial cross-sectional view of a device constructed in accordance with yet another embodiment of the invention.

Devices 250D, 250E constructed in accordance with alternative embodiments of the present invention are shown in FIGS. 27 and 28. The devices 250D, 250E are similar in structure and function to the devices 250B, 250C shown in FIGS. 25 and 26. However, the devices shown in FIGS. 27 and 28 have deeper and more angular-shaped recesses. Consequently, the outwardly facing recess of the rim 252E may provide a substance-containing space 406' whose volume is easier to visualize and control. The inwardly facing recess 408' of the rim 252D provides the same advantage and also provides for a more positive engagement or interlocking between compressed portions of the rim 252D during insertion of the device 250D.

Each of the devices illustrated in FIGS. 1 through 18 and 22 through 28 may be used to deliver therapeutic agents, such as drugs, into the vaginal canal 201. The substances to be delivered may be impregnated into the device so as to be slowly released while the device is positioned within the canal. The substance may be impregnated into the device by mixing the substance or its precursors into the material of the device prior to formation of the device. Alternatively, the substance may be injected or absorbed into one or more portions of the device after the device has been formed. The substance may also be coated onto one or more portions of the collection devices.

Substances that can be delivered intravaginally by the present invention include timed-release and bolus released, systemic and topical, medicants for all diseases of the vagina and other reproductive organs and any and all diseases of the entire female anatomy where vaginal delivery can be utilized for both menstruating and non-menstruating females. For example, medication for the treatment of yeast and fungal infections can be delivered intravaginally without interruption even during menstruation. The invention may also be used for the delivery of deodorizing materials for odor prevention, for the delivery of lubrication and for the delivery of steroids, hormones, antibacterial agents, and other pharmacological, chemical, natural and homeopathic agents. The invention may also be used for intravaginal delivery of anesthetic for local and general surgical procedures and for the delivery of pain relieving medication for intermittent and chronic pain.

Figure 19:
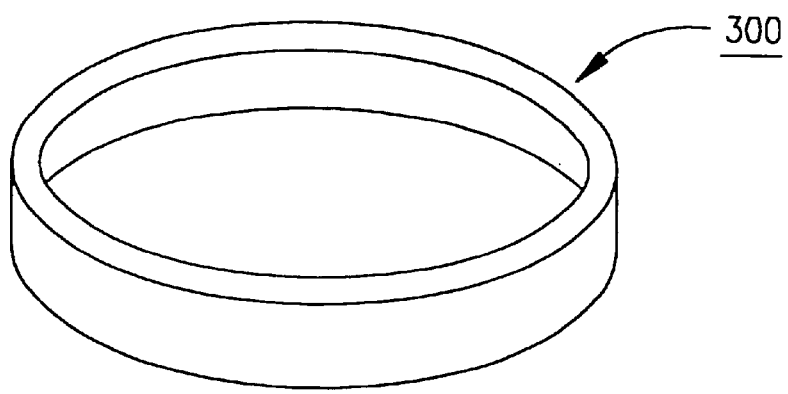
FIG. 19 is a perspective view of an intravaginal drug delivery ring according to the present invention.
Figure 20:
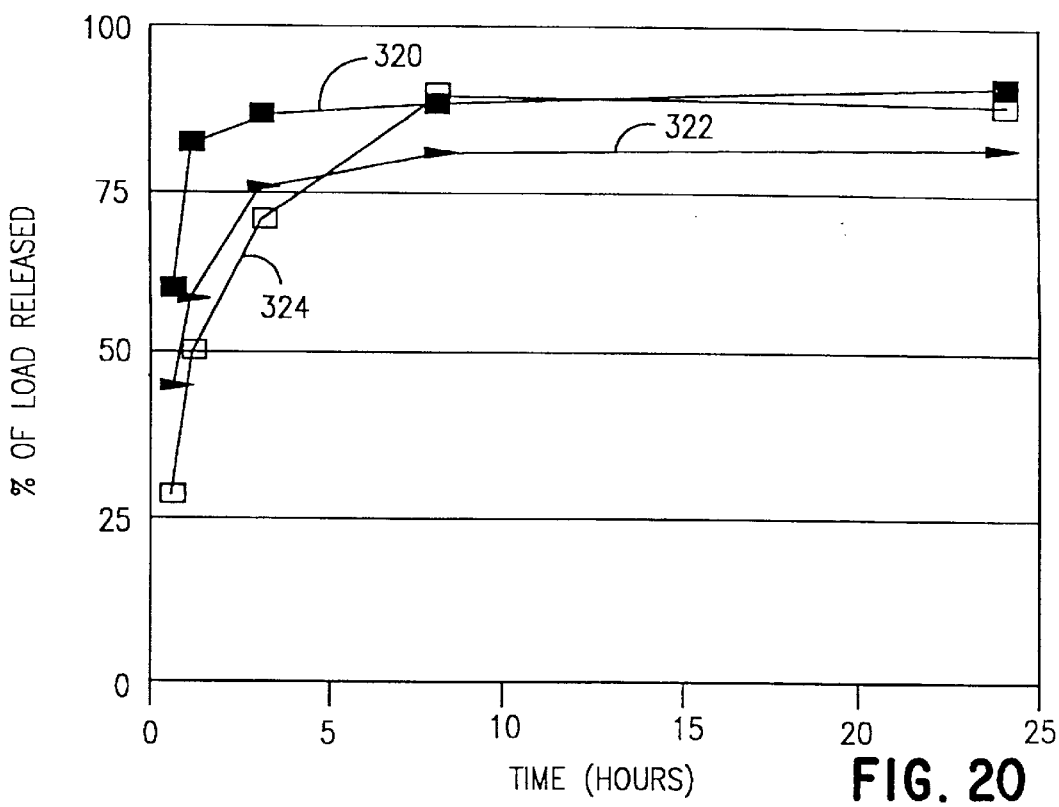
FIG. 20 illustrates the percentage of metronidazole released from KRATON® films containing 0.100, 0.500 and 1.000 gram metronidazole.
Figure 21:
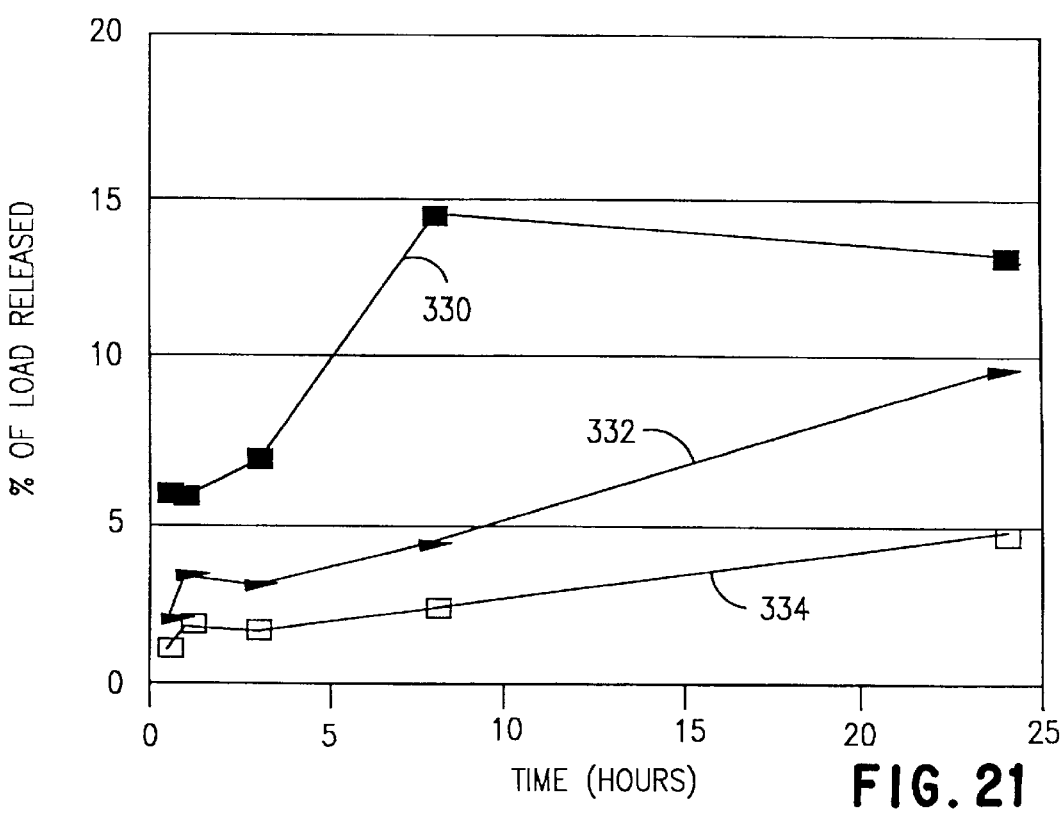
FIG. 21 illustrates the percentage of miconazole nitrate released from KRATON® films containing 0.100, 0.500 and 1.000 gram miconazole nitrate.

The above-described drugs and other substances do not necessarily have to be impregnated or absorbed into or coated on and delivered intravaginally by the devices illustrated in FIGS. 1 through 18, 22 and 23. The drugs and other substances may be delivered intravaginally by the drug delivery ring 300 illustrated in FIG. 19. The ring 300 fits within the vaginal canal 201 just like the rim 252 illustrated in FIG. 14, and the composition and dimensions of the drug delivery ring 300 may be identical to those of the rim 252. Therefore, the drug delivery ring 300 has the ergonomic advantages (convenience, comfort and reliability) of the rim 252. Since the ring 300 does not have a reservoir 254, it may be preferable to construct the ring 300 such that it has a compressed hoop strength of up to approximately seven hundred grams. The rim may have any of the cross-sectional configurations discussed and would then have the advantages associated with the configurations.

Moreover, one or more membranes can be provided to augment the utility of the ring 300 as a drug delivery device. For example, a drug-impregnated ring may have a membrane attached to its lower edge, thereby providing for collection of discharge caused by an infection. The attached membrane may itself be filled, coated or impregnated with a substance to be delivered intravaginally. Indeed, such a reservoir membrane may provide extra surface area, which is desirable for certain drug delivery modes. Or, permeable membranes may be stretched over the upper and lower edges of the ring, forming a drum-like structure.

The following examples demonstrate controlled delivery of substances from KRATON® films. The drug-impregnated films of the examples were cast from a solvent and closely approximate the dimensions (thickness, surface area, shape) of the reservoir 254.

EXAMPLE A

A 10% (w/v) solution of KRATON® elastomer in a suitable solvent was prepared. To 10 milliliters of this solution was added either 0.100, 0.500, or 1.000 gram of metronidazole (2-methyl-5-nitroimidazole-1-ethanol), an antiprotozoal used in the treatment of bacterial vaginosis. The mixture was vortexed to produce a homogeneous suspension, and then poured into glass molds. Upon evaporation of the solvent, the resulting films were composed of 1 gram elastomer and either 0.10, 0.50, or 1.00 gram of metronidazole distributed throughout the elastomer. The films were approximately 0.3 millimeter thick and provided a surface area of approximately 65 $cm^2$. The films were placed in a sealed jar containing a volume of simulated vaginal fluid and shaken gently at 37° C. for 24 hours. Samples of the fluid were removed at set time intervals and analyzed quantitatively for metronidazole by high performance liquid chromatography (HPLC).

The invention is not limited to the preferred embodiments described herein. For example, the invention is not restricted to human use. The invention may be used to collect discharge from non-human primates and other animals, and/or for substance delivery for veterinary applications. For non-human primate and other veterinary uses, the dimensions of the devices would be sized or adapted to fit the dimensions of the vaginal canal of the animal concerned.

In its broadest aspects, the invention is not limited to the collection of menstrual fluid. The invention may be used as a specimen collector to collect blood and/or vaginal, cervical and/or uterine discharge, including for diagnostic purposes.

The above description and drawings are only illustrative of preferred embodiments of the present invention, and it is not intended that the present invention be limited thereto. Any modification of the present invention which comes within the spirit and scope of the following claims is to be considered part of the present invention.

What is claimed is:

1. An intravaginal substance delivery system, said system comprising:
    a substance for intravaginal delivery; and
    a device for supporting said substance, said device being compressible from a first configuration to a low profile insertion configuration, said device including a rim for elastomerically restoring said device to said first configuration, the height of said rim being greater than the thickness of said rim; and
    wherein said rim is arranged to provide an outward holding force to hold said device in position during the intravaginal delivery of said substance; and
    wherein the height of said rim is no less than approximately five millimeters and no more than approximately fifteen millimeters.

2. The system of claim 1, wherein said rim is formed of thermoplastic material to provide a comfortable fit, said material being substantially softer at body temperature than at room temperature.

3. The system of claim 1, wherein said substance is coated onto the surface of at least a portion of said device.

4. The system of claim 1, wherein said substance is injected into at least a portion of said device.

5. The system of claim 1, wherein said substance is mixed during manufacturing of said device.

6. The system of claim 1, wherein said substance includes a therapeutic agent impregnated into said rim.

7. The system of claim 1, wherein said substance is a spermicide.

8. The system of claim 1, wherein said substance is a virucide.

9. The system of claim 1, wherein said substance is an anti-bacterial agent.

10. The system of claim 1, wherein said rim has an outer diameter in said first configuration of no less than approximately sixty millimeters and no more than approximately eighty millimeters.

11. The system of claim 1, wherein said rim has a substantially D-shaped configuration.

12. The system of claim 11, wherein said rim has a substantially flat surface for improved handling.

13. The system of claim 1, wherein said rim has a substantially figure-eight-shaped cross-sectional configuration.

14. The system of claim 13, wherein said rim has a recessed portion containing said substance.

15. The system of claim 1, wherein said rim includes O-rings.

16. The system of claim 15, wherein said rim has a substantially B-shaped configuration.

17. The system of claim 16, wherein said rim has a recessed portion containing said substance.

18. The system of claim 1, wherein said rim includes latex rubber.

* * * * *